Sept. 26, 1939. W. I. JOHNSTON Plant Pat. 341
ROSE PLANT
Filed Dec. 17, 1938
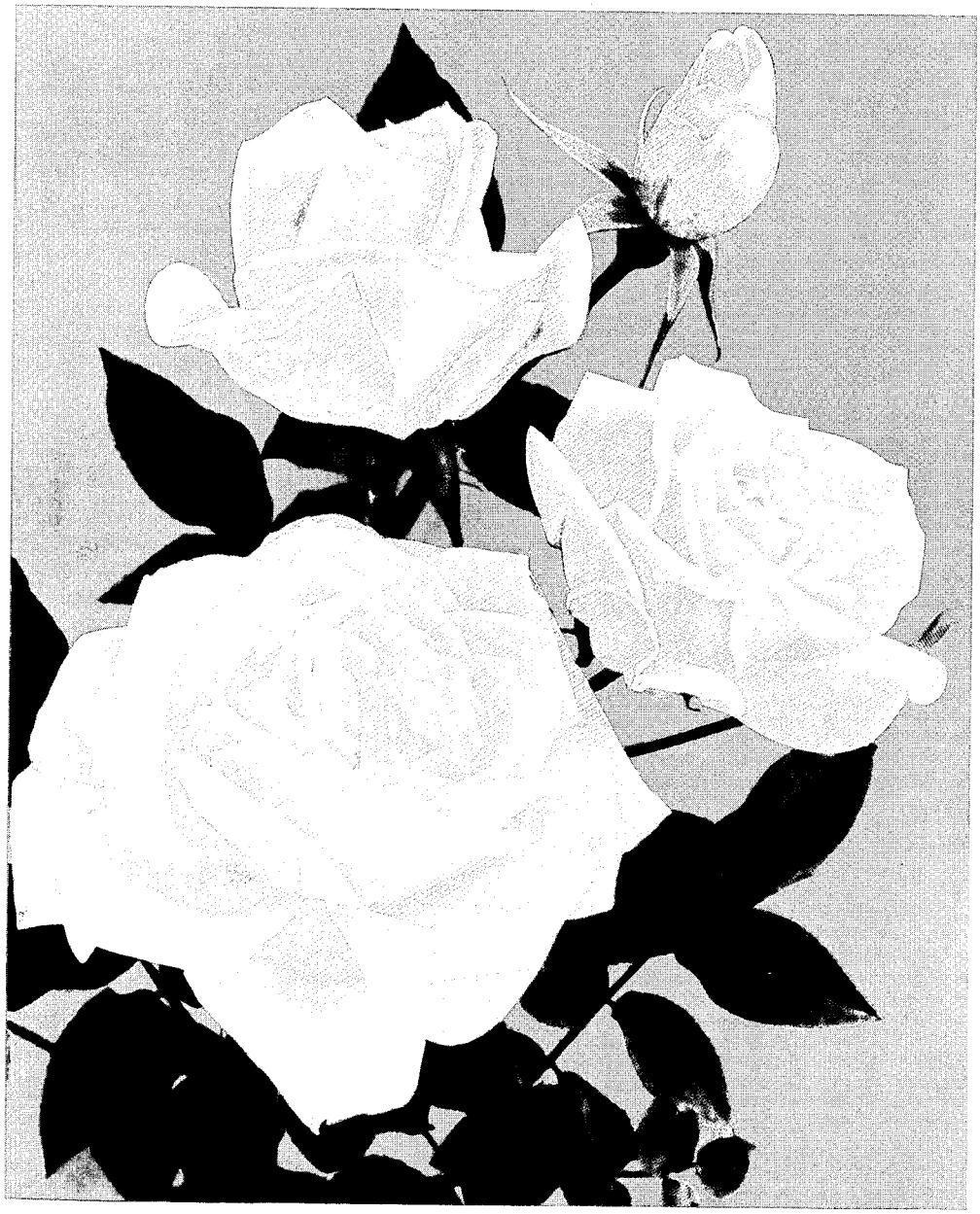
Inventor
Walter Irwin Johnston
By Robert Robb
Attorney Patented Sept. 26, 1939

Plant Pat. 341

UNITED STATES PATENT OFFICE

341

ROSE PLANT

Walter Irwin Johnston, Portadown, Ireland, assignor to Jackson & Perkins Company, Newark, N. Y.

Application December 17, 1938, Serial No. 246,470

1 Claim. (Cl. 47—61)

This invention relates to a new and distinct variety of Hybrid Tea rose plant, the result of a definite effort to breed into a Pink Hybrid Tea rose desirable and unusual characters for the color as well as desirable shades and tones of the color.

The distinctiveness of the variety is due to the very free flowering for a double Pink rose of its size, as well as the retention of the clearness of the color until the petals drop.

A further novel characteristic of importance is found in the texture of the petal which makes it very resistant to heat, sun and frost.

The plant has been asexually reproduced and its distinguishing characteristics have been found to be fixed.

The following is a detailed description of the new variety, all color terminology being in accordance with Ridgway's Color Standard:

Classification:

*Botanic and commercial.*—Hybrid Tea.

*Flower*

(Observations made at Newark, New York, in the morning of June 23rd, 1938.)

Blooming Habit:

Recurrent—continuous.

Bud:

*Size.*—Medium.

*Form.*—Pointed; ovoid; is not affected by wet or hot weather.

*Color.*—When sepals first divide—Plate 1, Begonia Rose. When petals begin to unfurl—Plate 1, Eosine Pink. When half blown: inside of petals—Plate 1, La France Pink; reverse of petals—Between Plate 12, Deep Rose Pink and Plate 1, Geranium Pink. Lower part suffused with Plate 5, Pale Greenish Yellow.

*Sepals.*—Serrated, branched in many specimens; curl back when opening.

*Calyx.*—Shape—apple; size—broad; aspect—smooth. Odor when rubbed—none.

*Peduncle.*—Length—long; aspect—prickly. Color—top: Plate 13, Acajou Red; bottom: Plate 31, Cress Green. Strength—erect, slender.

*Opening.*—Bud opens well; is not affected by adverse conditions.

Bloom:

*Size.*—Medium.

*Average size when fully expanded.*—Four and one-half inches.

*Borne.*—Singly.

*Stems.*—Medium length, normal.

*Form.*—When first open—high center. Permanence—outer petals curl back; like a show dahlia.

*Petalage.*—Double (full but open center). Number of petals under normal conditions—52.

*Color.*—Center of flower—Plate 1, La France Pink; outer petals—Plate 1, Hermosa Pink—slight indications of Plate 12, Rose Pink; base of petals (aiglet)—Plate 5, Light Greenish Yellow; inside of petals—Plate 1, La France Pink; reverse of petals—Plate 12, Rose Pink; general tonality from a distance—Salmon color.

*Discoloration.*—General tonality at end of first day—Plate 1, La France Pink; second day—Plate 1, Hermosa Pink; third day—Plate 12, Rose Pink.

Petals:

*Texture.*—Thick; is not affected by wet or hot weather.

*Appearance.*—Inside—satiny; outside—shiny.

*Form.*—Oval, notched.

*Arrangement.*—Irregular.

*Persistence.*—Drop off cleanly.

*Fragrance.*—Slight; nature—Sweet Briar.

*Lasting quality.*—On the plant—very long; as cut flower—long.

Genital organs:

*Stamens, anthers.*—Medium size; many. Color—Plate 5, Pale Greenish Yellow. Arrangement—regular around styles.

*Stamens, filaments (threads).*—Medium size; color—Plate 5, Sulphur Yellow.

*Pollen.*—Plate 4, Apricot Yellow.

*Styles.*—Loosely separated; uneven length; medium length; thin.

*Stigmas.*—Plate 4, Baryta Yellow.

*Ovaries.*—All enclosed in calyx.

Fruit:

Variety is fertile with its own pollen.

*Form.*—Ovoid.

*Aspect.*—Smooth.

*Sepals.*—Permanent; recurved.

*Plant*

Form:

Bush.

Growth:

Vigorous, branching.

Foliage:

5 to 7 leaflets.

*Size.*—Medium.

*Quantity.*—Normal.

*Color.*—New foliage: upper side—Plate 13, Hay's Maroon; mid-rib—Plate 31, Cress Green; under side—Plate 13, Vandyke Red. Old foliage: upper side—Plate 31, Cress Green; under side—Plate 31, Light Cress Green.

*Shape.*—Oval pointed.

*Texture.*—Upper side—glossy; under side—smooth. Ribs and veins—ordinary. Edge—serrated (saw toothed). Serration—double, small. Rachis: color—Plate 31, Cress Green; under side—prickles.

*Stipules.*—Medium length; smooth.

*Disease resistance.*—Susceptible to black spot.

Wood:

*New wood.*—Color—Plate 13, Vandyke Red; bark—rough.

*Old wood.*—Color—Plate 31, Cress Green; bark—smooth.

Thorns (divided into thorns, prickles and short needles):

*Thorns.*—Quantity: on main stalks from base—ordinary; on laterals from stalk—ordinary. Form—broad base, medium length. Color when young—Plate 13, Acajou Red. Position—irregular.

*Prickles.*—Quantity: on main stalks—few; on laterals—many. Color—Plate 13, Acajou Red.

*Short needles.*—Quantity: on main stalks and laterals—few.

I claim:

A new and distinct variety of Hybrid Tea rose plant, characterized as to novelty by the free flowering and double pink coloring of its large size flowers, retention of the clarity of said coloring until dropping off of the petals, and the resistant texture of said petals, substantially as shown and described.

WALTER IRWIN JOHNSTON.